United States Patent [19]

Wollweber

[11] Patent Number: 4,965,363
[45] Date of Patent: Oct. 23, 1990

[54] PROCESS FOR THE PREPARATION OF 3-CYANO-4-ARYL-PYRROLES

[75] Inventor: Detlef Wollweber, Wuppertal, Fed. Rep. of Germany

[73] Assignee: Bayer Aktiengesellschaft, Leverkusen, Fed. Rep. of Germany

[21] Appl. No.: 293,720

[22] Filed: Jan. 5, 1989

[30] Foreign Application Priority Data

Jan. 9, 1988 [DE] Fed. Rep. of Germany ....... 3800387

[51] Int. Cl.$^5$ ................. C07D 207/34; C07D 401/04; C07D 409/04; C07D 405/04
[52] U.S. Cl. .................................... 548/561; 546/281; 548/517; 548/526; 548/527
[58] Field of Search ........................... 548/561, 526

[56] References Cited

U.S. PATENT DOCUMENTS 4,680,413 7/1987 Genda et al. .................... 548/526

FOREIGN PATENT DOCUMENTS 0182738 5/1986 European Pat. Off. .
2927480 1/1980 Fed. Rep. of Germany .

OTHER PUBLICATIONS

Zabicky, J. Chem Soc. 1961, 683.
Greenlee, J. Org. Chem. 46, 5351–5353 (1981).
Derwent for JP-61-030571.

Primary Examiner—Mark L. Berch
Attorney, Agent, or Firm—Sprung Horn Kramer & Woods

[57] ABSTRACT

A process for the preparation of a 3-cyano-4-arylpyrrole of the formula

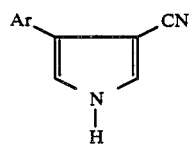

(I)

in which
Ar is optionally substituted heteroaryl or aryl, comprising reacting an α-cyanocinnamamide of the formula

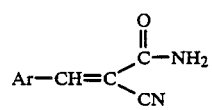

(II)

with a sulphonylmethylisocyanide of the formula $$R-SO_2-CH_2-NC$$ (III)

in which
R is alkyl, optionally substituted cycloalkyl or optionally substituted aryl, in the presence of a base and in the presence of a diluent.

The products are known fungicides.

7 Claims, No Drawings

PROCESS FOR THE PREPARATION OF 3-CYANO-4-ARYL-PYRROLES

The invention relates to a new process for the preparation of 3-cyano-4-aryl-pyrroles, which are known as fungicides.

It is known that 3-cyano-4-aryl-pyrroles are obtained when cinnamonitriles are reacted with p-toluenesulphonylmethylisocyanide in the presence of sodium hydride (cf. DE-OS No. (German Published Specification) No. 2,927,480). However, with a yield of about 35%, the results of this process are not satisfactory. Another disadvantage is that the purification of the compounds which can be obtained in this manner is complicated (cf. J6-1030-571). Finally, the sodium hydride which is used as reagent is unsuitable for industrial syntheses because of its high susceptibility to hydrolysis and the associated danger of fire which the gaseous hydrogen liberated during hydrolysis entails.

Furthermore, it is also known that 3-cyano-4-aryl-pyrroles are also obtained when α-cyanocinnamic acid esters or α-cyanocinnamic acids are reacted with p-toluenesulphonylmethylisocyanide in the presence of bases and if appropriate in the presence of copper(II) salts (cf. J6-1030-571 or J6-1200-984 and U.S. Pat. No. 4,680,413). A disadvantage in this process is that the α-cyanocinnamic acid esters required as starting compounds must first be prepared in a complicated process (cf. J. chem. Soc. -1961, 683).

In addition, it is known that 3-cyano-4-aryl-pyrroles are also obtained when α-substituted cinnamonitriles are cyclized with ethyl isocyanoacetate in the presence of sodium hydride and the resulting pyrrole-2-carboxylic acid esters are hydrolysed with bases and then thermically decarboxylated (cf. JP 59/212 468). Again, the disadvantageous properties of sodium hydride prohibit the applicability of this process in industry. Also, the yields of the cyclization step are not satisfactory at a level of 44%.

Furthermore, it is known that 3-cyano-4-aryl-pyrroles are obtained when phenacylamine derivatives are reacted with suitably substituted acrylonitrile derivatives (cf. EP 174,910). However, the phenacylamine derivatives required as starting compounds are only available via a complex, multi-step synthesis the course of which, inter alia, also requires the unpleasant use of cyanides.

Furthermore, it is known that 3-cyano-4-aryl-pyrroles are obtained when the corresponding 3-trifluoromethyl-4-aryl-pyrroles are reacted with ammonia at an elevated temperature and at elevated pressure (cf. EP 182 738). However, in this process, too, the 3-trifluoromethyl-4-aryl-pyrroles required as starting materials are only available via a complex, multi-step path, the use of moisturesensitive "Wittig reagents" and expensive trifluoroacetic anhydride in the course of this multi-step synthesis making the industrial feasibility even more difficult.

Finally, it is known that 3-cyano-4-aryl-pyrroles are obtained when 3-cyano-4-aryl-Δ²-pyrrolines are oxidized in the presence of Cu(II) salts or iron(III) salts (cf. EP 183,217). In this last process, the starting compounds required are also prepared in a multi-step process and in a complex procedure.

It has been found that 3-cyano-4-aryl-pyrroles of the general formula (I)

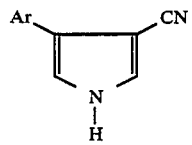

in which
  Ar stands in each case for optionally substituted heteroaryl or aryl,
are obtained when α-cyanocinnamamides of the formula (II)

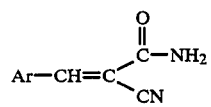

in which
  Ar has the abovementioned meaning, are reacted with sulphonylmethylisocyanides of the formula (III)

in which
  R stands for alkyl, for optionally substituted cycloalkyl or for optionally substituted aryl,
in the presence of a base and in the presence of a diluent.

It must be considered as extremely surprising that, by the process according to the invention, the desired 3-cyano-4-aryl-pyrroles of the general formula (I) are obtained in good yields of between 91 and 94% and in a high purity, since, according to what was known from the prior art, both possible reaction paths which could lead to the final product could not be considered as obvious. On the one hand, it could not be expected that the hydrolysis of an amide grouping and the subsequent decarboxylation would proceed under such mild conditions (cf., for example, J org. Chem. 46, 5351–5353 [1981]). On the other hand, the alternative direct splitting-off of a carbon-amide group with the release of isocyanic acid has not hitherto been described in the literature.

From the prior art, it would rather have been expected that the anions occurring as intermediates, of the formula (IV)

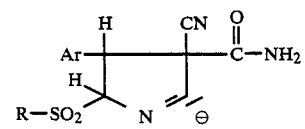

in which
  R and Ar have the abovementioned meanings, would stabilize themselves by splitting off sulphinates to give the 3-H-pyrroles of the formula (V)

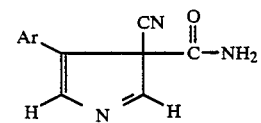

in which

Ar has the abovementioned meaning from which the amide grouping would not be selectively detachable without difficulties (cf. U.S. Pat. No. 4,680,413).

Compared to the most similar prior art (U.S. Pat. No. 4,680,413), the process according to the invention has the advantage that the α-cyanocinnamamides of the formula (II) used as starting materials can be prepared under much milder conditions than, for example, the corresponding α-cyanocinnamic acid esters (cf., for example, J. chem. Soc. 1961, 683) and moreover are much less sensitive at higher temperatures where the corresponding α-cyanocinnamic acid esters or the corresponding free acids are already prone to premature decarboxylation.

Formula (I) provides a general definition of the 3-cyano-4-aryl-pyrroles which can be obtained with the aid of the process according to the invention.

The compounds of the formula (I) which can preferably be prepared are those in which Ar stands for pyridyl, furyl or thienyl, each of which is optionally monosubstituted or polysubstituted by identical or different substituents from the series comprising halogen and straight-chain or branched alkyl having 1 to 4 carbon atoms, or stands for phenyl which is optionally monosubstituted or polysubstituted by identical or different substituents, suitable substituents being: halogen, cyano, nitro, in each case straight-chain or branched alkyl, alkoxy, alkylthio or alkoxycarbonyl, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms, and doubly-linked dioxyalkylene having 1 or 2 carbon atoms which is optionally substituted by fluorine.

Compounds of the formula (I) which can be particularly preferably prepared are those in which Ar stands for 2-pyridyl, 4-pyridyl, 2-furyl or 2-thienyl, each of which is optionally monosubstituted, disubstituted or trisubstituted by identical or different substituents from the series comprising fluorine, chloride, bromine, methyl and ethyl, or stands for phenyl which is optionally monosubstituted, disubstituted or trisubstituted by identical or different substituents, suitable substituents being: fluorine, chlorine, bromine, methyl, ethyl, n- or i-propyl, methoxy, ethoxy, methylthio, trifluoromethyl, trifluoromethoxy, trifluoromethylthio, cyano, nitro, dioxymethylene and dioxydifluoromethylene.

Compounds of the formula (I) which can be very particularly preferably prepared are those in which Ar stands for phenyl which is optionally monosubstituted, disubstituted or trisubsituted by identical or different substituents, suitable substituents being: fluorine, chlorine, bromine, methyl, ethyl, methoxy, ethoxy, methylthio, trifluoromethyl, trifluoromethoxy, trifluoromethylthio, nitro and dioxydifluoromethylene.

If, for example, 2-(2,3-dichlorophenyl-methylidene)-cyanacetamide and p-toluenesulphonylmethyl isocyanide are used as starting substances, the course of the reaction of the process according to the invention may be represented by the following equation:

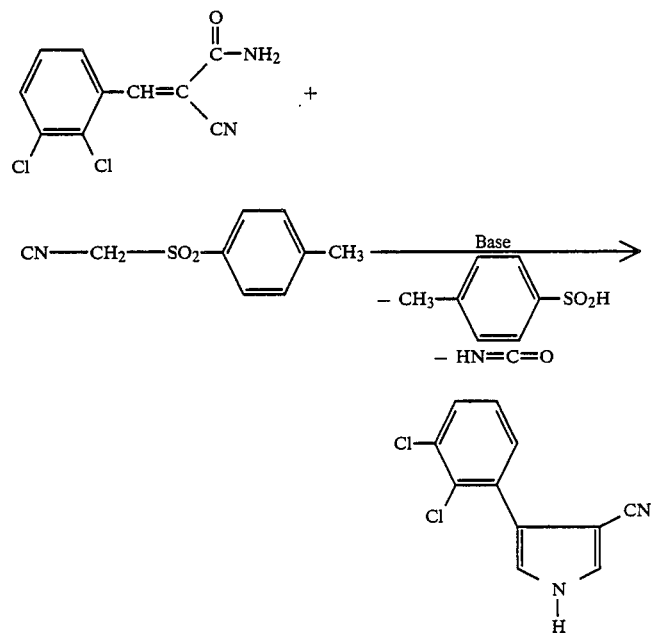

Formula (II) provides a general definition of the α-cyanocinnamamides required as starting substances for carrying out the process according to the invention. In this formula (II), Ar preferably stands for those radicals which have already been mentioned in connection with the description of the substances of the formula (I) according to the invention as being preferred for these substituents.

The α-cyanocinnamamides of the formula (II) are known or can be obtained in analogy to known processes (cf., for example, J. chem. Soc. 1961, 683), for example by subjecting aldehydes of the formula (VI)

in which

Ar has the abovementioned meaning, to a condensation reaction with α-cyanacetamide of the formula (VII)

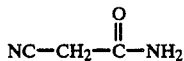
(VII)

at temperatures of between +20° C. and +150° C., if appropriate in the presence of a diluent, such as, for example, ethanol, and if appropriate in the presence of a base, such as, for example, potassium hydroxide or piperidine.

The aldehydes of the formula (VI) and the α-cyanacetamide of the formula (VII) are generally known compounds of organic chemistry or can be obtained in analogy to known processes.

Formula (III) provides a general definition of the sulphonylmethylisocyanides furthermore required as starting substances for carrying out the process according to the invention. In this formula (III), R preferably stands for straight-chain or branched alkyl having 1 to 4 carbon atoms, for cycloalkyl which has 3 to 7 carbon atoms and is optionally monosubstituted or polysubstituted by straight-chain or branched alkyl having 1 to 4 carbon atoms and/or halogen, or for aryl which has 6 to 10 carbon atoms and is optionally monosubstituted or polysubstituted by identical or different substituents, suitable substituents being; halogen, cyano, nitro, in each case straight-chain or branched alkyl, alkoxy or alkylthio, each having 1 to 4 carbon atoms, in each case straight-chain or branched halogenoalkyl, halogenoalkoxy or halogenoalkylthio, each having 1 to 4 carbon atoms and 1 to 9 identical or different halogen atoms. R particularly preferably stands for methyl, cyclohexyl or for phenyl or naphthyl, each of which is optionally monosubstituted, disubstituted or trisubstituted by identical or different substituents, suitable substituents in each case being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy and trifluoromethylthio.

The sulphonylmethylisocyanides of the formula (III) are known or can be obtained in analogy to known processes (cf., for example, DE-OS (German Published Specification) No. 3,601,285; U.S. Pat. No. 4,680,413; Tetrahedron Lett. 1972, 2367–2368; J. Org. Chem. 42, 1153–1159 [1977]; Synthesis 1985, 400–402; Organic Syntheses 57, 102–106 [1977]).

Suitable diluents for carrying out the process according to the invention are inert organic solvents. These include in particular aliphatic, alicyclic or aromatic hydrocarbons, optionally halogenated, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl or diethyl ether, or alcohols, such as methanol, ethanol, propanol or butanol.

The process according to the invention is carried out in the presence of a suitable base. Suitable bases are all inorganic and organic bases which can be used customarily. The hydrides, hydroxides, amides, alkoxides, carbonates or hydrogen carbonates of alkali metals, such as, for example, sodium hydride, sodium amide, sodium hydroxide, sodium methoxide, sodium ethoxide, potassium tbutoxide, sodium carbonate or sodium hydrogen carbonate, are preferably used.

When carrying out the process according to the invention, the reaction temperatures may be varied within a relatively wide range. In general, the process is carried out at temperatures of between −30° C. and +100° C., preferably at temperatures of between −10° C. and +40° C.

For carrying out the process according to the invention, 1.0 to 2.0 moles, preferably 1.0 to 1.3 moles, of sulphonylmethylisocyanide of the formula (III) and 1.0 to 6.0 moles, preferably 1.0 to 3.0 moles, of base are generally employed per mole of α-cyanocinnamamide of the formula (II). In this process, a procedure is followed in which the α-cyanocinnamamide of the formula (II) is initially taken in a suitable solvent together with the base, the sulphonylmethylisocyanide of the formula (III) which is dissolved in a suitable solvent is then added dropwise, the mixture is then stirred at the reaction temperature for several hours, any organic solvent is removed in vacuo, and the residue is treated with water, with the desired 3-cyano-4-aryl-pyrroles of the formula (I) being obtained as a precipitate and all the by-products remaining dissolved. By filtering and drying, very pure products are obtained in high yield.

The resulting 3-cyano-4-aryl-pyrroles are known fungicides (cf., for example, EP 236,272) or important intermediates for fungicides (cf., for example, U.S. Pat. No. 4,680,413), DE-OS No. (German Published Specification) 2,927,480 or EP 182,737).

PREPARATION EXAMPLES

EXAMPLE 1

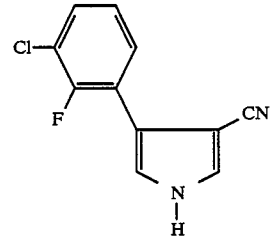

A solution of 0.95 g (0.041 mole) of sodium in 20 ml of ethanol is added to 6.75 g (0.03 mole) of 2-(2-fluoro-3-chlorophenyl-methylidene)-cyanacetamide in 40 ml of ethanol at 0° C. to 5° C., a solution of 7.0 g (0.036 mole) of p-toluenesulphonylmethylisocyanide in 50 ml of dichloromethane is then added dropwise and with stirring, also at 0° C. to 5° C; when the addition is complete, the batch is stirred for 1 hour at 0° C. and for 3 hours at room temperature, 30 ml of water are then added, the pH is adjusted to 3 using 1 normal hydrochloric acid, any organic solvent is removed in vacuo, a further 60 ml of water are added, the mixture is stirred for 30 minutes at room temperature, and the resulting solid is filtered off with suction and dried.

6.2 g (94% of theory) of 3-cyano-4-(2-fluoro-3-chlorophenyl)-pyrrole of melting point 180° C.–181° C. are obtained.

Preparation of the starting compound

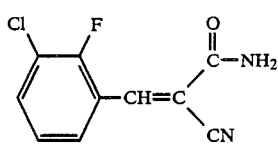

52.3 g (0.62 mole) of cyanacetamide and 3 g (0.05 mole) of potassium hydroxide are added in succession to 98.3 g (0.62 mole) of 2-fluoro-3-chlorobenzaldehyde (cf. DE-OS No. (German Published Specification) 3,129,277) in 500 ml of ethanol, and the mixture is then stirred at room temperature for 15 hours. The precipitated solids are filtered off with suction and dried.

91.6 g (66% of theory) of 2-(2-fluoro-3-chlorophenyl-methylidene)-cyanacetamide of melting point 160° C.-162° C. are obtained.

The following 3-cyano-4-aryl-pyrroles of the general formula (I) are obtained in a corresponding manner and in accordance with the general data for the preparation:

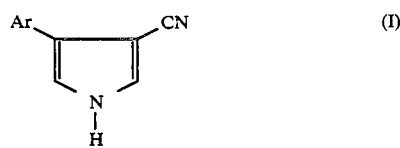

| Example No. | Ar | Yield | Melting point (°C.) |
|---|---|---|---|
| 2 | Cl, Cl | 93% | 139–141 |
| 3 | Cl, F, F | 91% | 218–219 |

It is understood that the modification and examples are illustrative but not limitative of the present invention and that other embodiments within the spirit and scope of the invention will suggest themselves to those skilled in the art.

I claim:

1. A process for the preparation of 3-cyano-4-(2-fluoro-3-chlorophenyl)-pyrrole of the formula

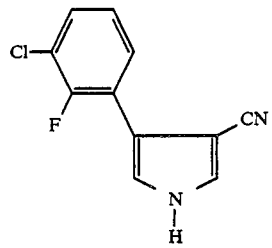

comprising (a) reacting 2-(2-fluoro-3-chlorophenyl-methylidene)cyanacetamide with a sulphonylmethylisocyanide of the formula

R—SO$_2$—CH$_2$—NC in which

R is alkyl, unsubstituted or substituted cycloalkyl or unsubstituted or substituted aryl, in the presence of a base and in the presence of a diluent, and (b) adjusting the pH to about 3 when the reaction is complete by adding hydrochloric acid.

2. A process according to claim 1, carried out at a temperature between about −30° C. and +100° C.

3. A process according to claim 1, carried out at a temperature between about −10° C. and +40° C.

4. A process according to claim 1, wherein about 1 to 2 moles of sulphonylmethylisocyanide and about 1 to 6 moles of base are employed per mole of α-cyanocinnamamide.

5. A process according to claim 1, wherein about 1 to 1.3 moles of sulphonylmethylisocyanide and about 1 to 3 moles of base are employed per mole of 60 -cyanocinnamamide.

6. A process according to claim 1, carried out at a temperature between about −10° C., and +40° C., about 1 to 1.3 moles of sulphonylmethyisocyamide and about 1 to 3 moles of base being employed per mole of 60 -cyanocinnamamide.

7. A process for the preparation of 3-cyano-4-(2-fluoro-3-chlorophenyl)-pyrrole of the formula

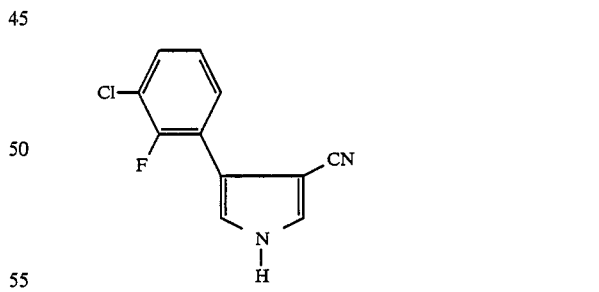

comprising
(a) reacting 2-(2-fluoro-3-chlorophenyl-methylidene)cyanacetamide in a solution of sodium and ethanol with p-toluenesulphonylmethylisocyanide in dichloromethane;
(b) adjusting the pH to about 3 when the reaction is complete by adding hydrochloric acid; and
(c) recovering the product.

* * * * *

UNITED STATES PATENT AND TRADEMARK OFFICE
CERTIFICATE OF CORRECTION

PATENT NO. : 4,965,363

DATED : October 23, 1990

INVENTOR(S) : Detlef Wollweber

It is certified that error appears in the above-identified patent and that said Letters Patent is hereby corrected as shown below:

Col. 8, lines 36 & 42    Delete " 60 " and substitute -- a --

Signed and Sealed this

Twenty-eighth Day of July, 1992

Attest:

DOUGLAS B. COMER

*Attesting Officer*     *Acting Commissioner of Patents and Trademarks*